United States Patent
Schramm et al.

(10) Patent No.: US 12,152,924 B2
(45) Date of Patent: Nov. 26, 2024

(54) SENSOR DEVICE AND METHOD FOR DETERMINING PROPERTIES OF A LIQUID

(71) Applicant: Kyocera AVX Components (Werne) GmbH, Werne (DE)

(72) Inventors: Daniel Schramm, Lunen (DE); Marco Rutkowski, Selm (DE); Gregory Sapsford, Werne (DE)

(73) Assignee: Kyocera AVX Components (Werne) GmbH, Werne (DE)

( * ) Notice: Subject to any disclaimer, the term of this patent is extended or adjusted under 35 U.S.C. 154(b) by 371 days.

(21) Appl. No.: 17/830,820

(22) Filed: Jun. 2, 2022

(65) Prior Publication Data

US 2022/0397441 A1 Dec. 15, 2022

(30) Foreign Application Priority Data

Jun. 11, 2021 (DE) .................... DE 102021115223.2

(51) Int. Cl.
*G01F 23/26* (2022.01)
*G01F 23/263* (2022.01)
(Continued)

(52) U.S. Cl.
CPC ......... *G01F 23/266* (2013.01); *G01N 27/226* (2013.01); *G01N 33/1833* (2013.01)

(58) Field of Classification Search
CPC ............ H01R 13/6335; H01R 13/7175; G01F 23/266; G01N 27/226; G01N 33/1833
See application file for complete search history.

(56) References Cited

U.S. PATENT DOCUMENTS 3,935,739 A 2/1976 Ells
4,418,569 A * 12/1983 Kuhnel ................. G01F 23/266
73/304 C (Continued)

FOREIGN PATENT DOCUMENTS

| CN | 106289450 A | * | 1/2017 | ........... G01F 23/266 |
| DE | 102014015188 | | 4/2015 | |
| GB | 2267571 A | * | 12/1993 | ........... G01N 27/221 |

OTHER PUBLICATIONS

International Search Report and Written Opinion for PCT/EP2022/065266, mailed on Sep. 27, 2022, 15 pages.

(Continued)

*Primary Examiner* — Francis C Gray
(74) *Attorney, Agent, or Firm* — Dority & Manning, P.A.

(57) ABSTRACT

Aspects of the present disclosure relate to a sensor device and a method for detecting properties of a liquid. In one example, the liquid is accommodated in an inner chamber. A capacitor arrangement in the inner chamber has spaced, opposing capacitor surfaces so that at least part of the liquid accommodated in the inner chamber is arranged between the capacitor surfaces. An evaluation device for supplying an output signal A depending on a capacitance value of the capacitor arrangement includes an excitation circuit and an evaluation circuit. The excitation circuit has at least one measuring resistor and an AC voltage source configured to apply an AC voltage to a series circuit including the measurement resistor and the capacitor arrangement. The evaluation circuit has an output supplying the output signal A by measuring a voltage across the capacitor arrangement.

12 Claims, 4 Drawing Sheets

(51) Int. Cl.
    *G01N 27/22*     (2006.01)
    *G01N 33/18*     (2006.01)

(56) References Cited

U.S. PATENT DOCUMENTS

| | | | |
|---|---|---|---|
| 4,743,901 A | | 5/1988 | Yamanoue et al. |
| 5,051,921 A | * | 9/1991 | Paglione ............... G01F 23/268 |
| | | | 73/304 C |
| 5,777,483 A | * | 7/1998 | Bailey .................. G01N 27/221 |
| | | | 324/686 |
| 6,269,693 B1 | | 8/2001 | Irion |
| 6,614,242 B2 | | 9/2003 | Matter et al. |

OTHER PUBLICATIONS

Muhammad et al., "A High Resolution Capacitive Sensing System of the Measurement of Water Content in Crude Oil", Sensors, 2014, vol. 14, No. 7, pp. 11351-11361.

\* cited by examiner

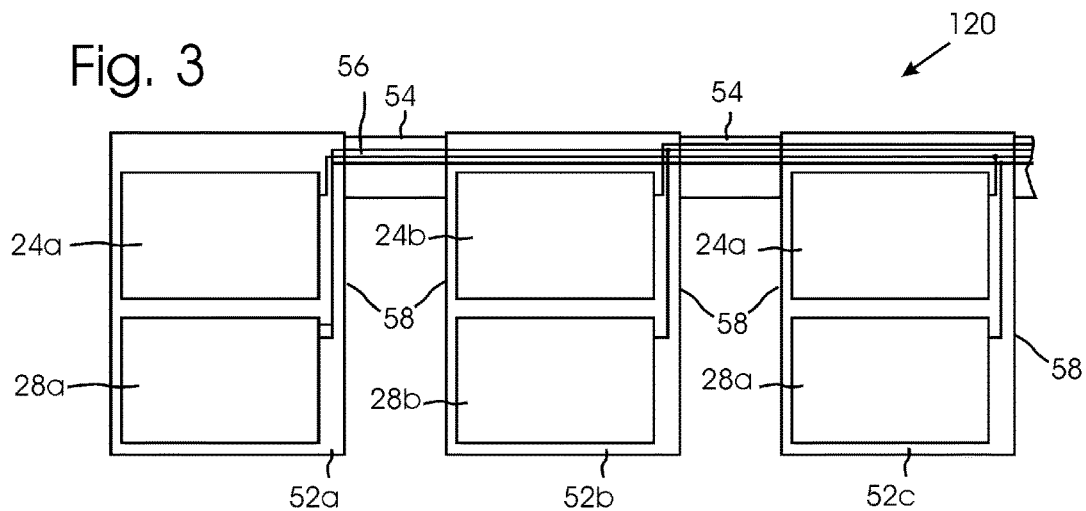
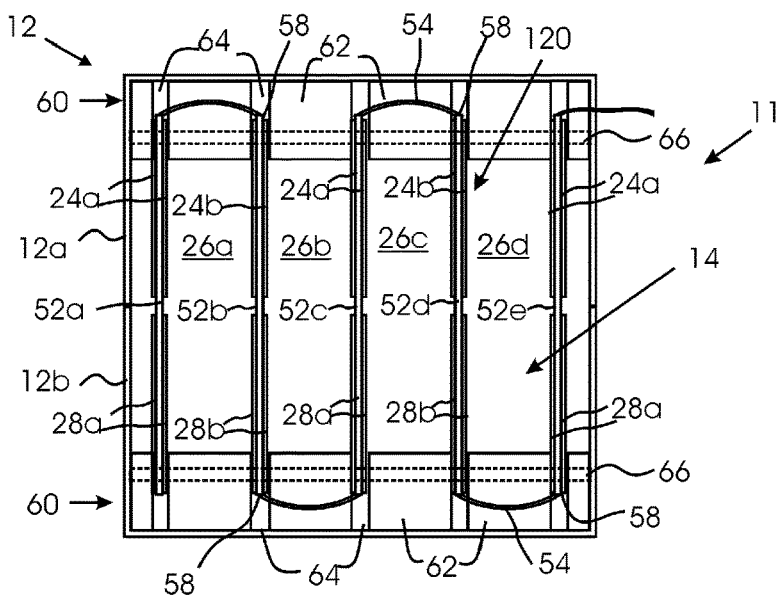
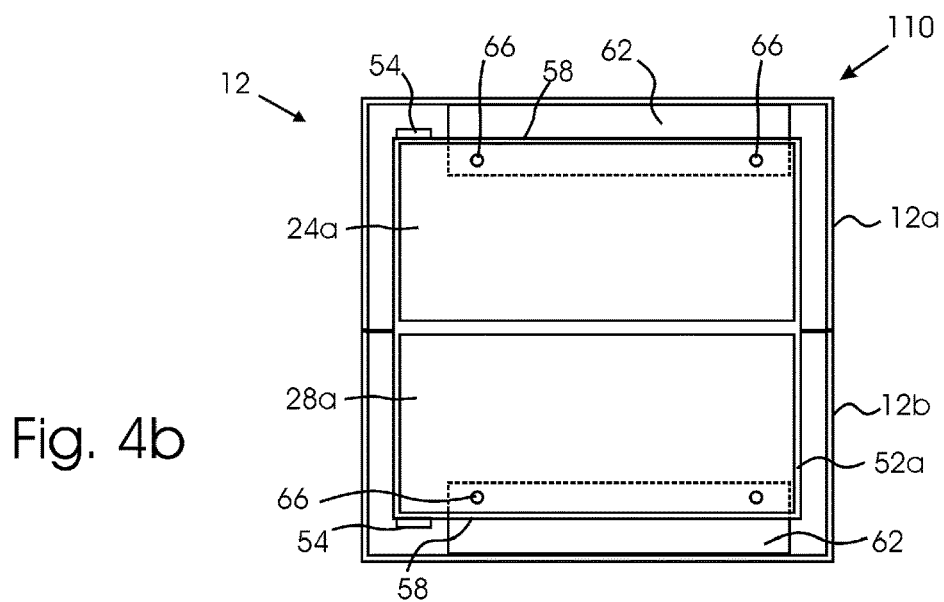

SENSOR DEVICE AND METHOD FOR DETERMINING PROPERTIES OF A LIQUID

PRIORITY CLAIM

The present application is based on and claims priority to German Application DE102021115223.2, entitled "Pedal Module with Actuator," having a filing date of Jun. 11, 2021 which is incorporated by reference herein.

FIELD

Example aspects of the present disclosure relate to a sensor device and a method for determining properties of a liquid. In particular, example aspects of the present disclosure relate to a device and a method for detecting properties of a liquid using a capacitive measuring principle.

BACKGROUND

U.S. Pat. No. 6,269,693 B1 describes a capacitive sensor for measuring a property of a fluid or a fill level of a fluid in a container. A printed circuit board is either flexible or has rigid and flexible sections. Metal coatings form capacitor plates on the PCB which is then bent so that two capacitor plates are held at a distance from each other by spacers so that they form a capacitor. Additional metal coatings are provided for shielding. Tracks on the PCB connect the capacitor plates to an evaluation circuit, and the shielding to a reference potential. The bent PCB is held in a housing and fixed by fixing pins.

EP 1 106 997 A2 describes a method and a device for oil-in-water measurement. In an electric measuring cell, a capacitance is measured as a measure of an oil concentration in water flowing through.

U.S. Pat. No. 4,418,569A discloses a device for the capacitive measurement of a level of filling having a measurement capacitor which dips into the fluids and a compensation capacitor dipping into the fluid. A circuit evaluates only the imaginary part of the complex conductance of the measurement capacitor and of the compensation capacitor, but not the real part thereof to achieve a measurement of the filling level independent of the material properties.

DE 2515065 A1 relates to a liquid level gauge for monitoring the height of liquid in a liquid storage, e.g. a liquid tank, with an upright conducting probe adapted to be immersed in the liquid in the tank, and an upright series of electrodes closely adjacent the probe. The latter is adapted to be excited from a source of a.c. voltage generated by an astable multivibrator. Each of the electrodes is connected to the input of an amplifier through a rectifier circuit. The amplifiers are of the digital comparator type and have output terminals respectively connected by means of summing resistors to an electrical indicator, which provides an indication of the number of amplifiers being driven to full output at any particular time. The arrangement is such that each of the electrodes constitutes one plate of a capacitor, the other plate being formed by the single upright conducting probe. When a particular electrode is above the level of fluid in the tank, the magnitude of the a.c. signal received at the electrode is of a sufficiently small magnitude to provide only a low level drive voltage to its respective comparator amplifier, the latter thus assuming a low output signal level. Once a particular plate becomes submerged, the increased dielectric constant (fluid) effects an increase in the value of the capacitor, and a correspondingly larger drive signal to the amplifier results, causing the output thereof to assume a high level and yielding a contribution to the meter reading through the respective summing resistor. The meter reading thus responds to the number of electrodes submerged at any particular time, and provides an indication of the liquid level in the tank.

U.S. Pat. No. 5,051,921 A describes a liquid level and composition sensor including a first interdigitated capacitor mounted substantially vertically in a tank, and a second interdigitated capacitor mounted substantially horizontally in and near the bottom of the tank. An electronic processor is responsive to the value of capacitance of the first capacitor for producing a first voltage signal proportional to the level of the liquid in the tank and is responsive to the value of capacitance of the second capacitor for producing a second voltage signal having a voltage level corresponding to the composition or dielectric constant of the liquid. The processor multiplies the first and second voltage signals together to produce a liquid level voltage output signal having a constant slope for voltage amplitude versus liquid level, regardless of the composition of the liquid in the tank.

SUMMARY

Aspects and advantages of embodiments of the present disclosure will be set forth in part in the following description, or may be learned from the description, or may be learned through practice of the embodiments.

One example aspect of the present disclosure is directed to a sensor device. The sensor device has an inner chamber for accommodating a liquid. The sensor device has a capacitor arrangement in the inner chamber. The capacitor arrangement has spaced, opposing capacitor surfaces so that at least part of the liquid accommodated in the inner chamber is arranged between the capacitor surfaces. The sensor device has an evaluation device for supplying an output signal that is at least dependent on a capacitance value of the capacitor arrangement. The evaluation device includes an excitation circuit and an evaluation circuit. The excitation circuit has at least one measuring resistor and an AC voltage source configured to apply an AC voltage to a series circuit. The series circuit includes the measuring resistor and the capacitor arrangement. The series circuit can form a low pass filter. The AC voltage has a frequency in a region of a cutoff frequency of the low pass filter. The evaluation circuit has an output configured to supply the output signal be measuring a voltage across the capacitor arrangement.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

FIG. 3 depicts a side view of a part of a PCB structure in an unfolded state according to example embodiments of the present disclosure;

FIGS. 4a and 4b depict a longitudinal section and cross-section of a sensor device with the PCB structure of FIG. 3 in a folded state according to example embodiments of the present disclosure;

DETAILED DESCRIPTION

Figure 1:
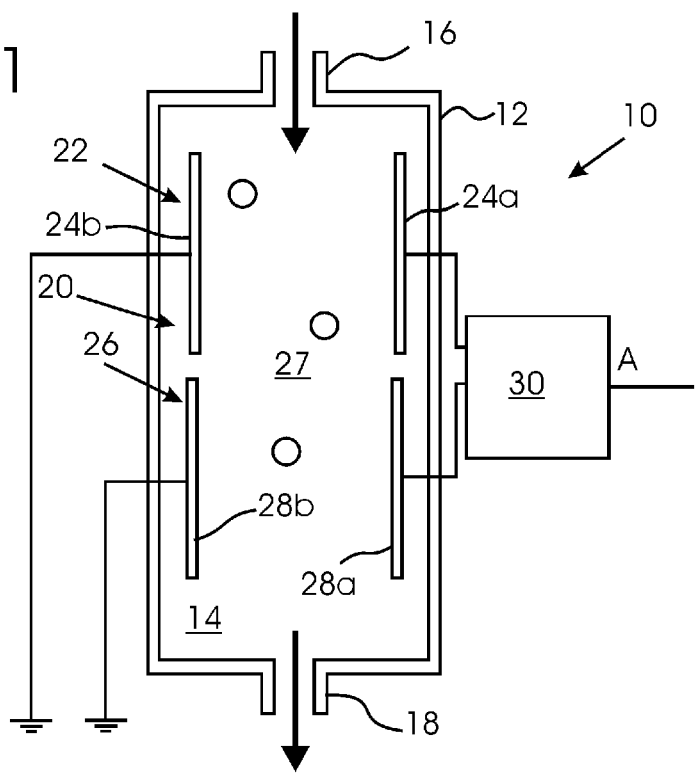
FIG. 1 depicts a schematic representation of a sensor device according to example embodiments of the present disclosure.

Aspects of the present disclosure are directed to a sensor device and a method for detecting properties of a liquid in which accurate detection is possible with simple means, in particular for the determination of water content in oil.

The sensor device according example aspects of the present disclosure has an inner chamber for accommodating a liquid and a capacitor arrangement in the inner chamber. The inner chamber can be formed within a housing. It can for example be a container or tank. In some embodiments, it is a piece of tube with an inlet and an outlet that are fluidically connected to each other across the inner chamber.

The capacitor arrangement comprises spaced, opposing capacitor surfaces with at least one gap so that at least part of the liquid accommodated in the inner chamber is arranged in the gap between the capacitor surfaces. The capacitor arrangement in some embodiments can form at least one measuring capacitance in which the liquid forms at least part of the dielectric.

According to example aspects of the present disclosure, an evaluation device is provided for supplying an output signal that is at least dependent on a capacitance value of the capacitor arrangement, such as on the capacitance value of at least one measuring capacitance formed thereby. The measuring capacitance can be part of a complex impedance. The evaluation device comprises an excitation circuit and an evaluation circuit. It should be noted that in this case, the concept of the circuit should be understood functionally and not necessarily structurally, i.e., the excitation circuit and evaluation circuit can be realized in whole or in part with the same components and/or use common circuit parts. Likewise, the evaluation device, the excitation circuit, and/or the evaluation circuit can have additional elements and/or functionalities. Given a possible complete or partial digital design of a circuit or circuit parts, for example a common processor can thus realize both parts of the functionality of the excitation circuit as well as the evaluation circuit, as well as other functionalities, if applicable.

According to example aspects of the present disclosure, the excitation circuit has at least one measuring resistor and an AC voltage source configured to supply an AC voltage to a series circuit including the measuring resistor and the capacitor arrangement, or respectively at least one measuring capacitance thereof. The capacitor arrangement, or respectively a measuring capacitance formed thereby, can for example be part of a complex impedance by way of circuitry, connected for example together with at least one measuring resistor as an RC element that is excited by an AC voltage with a suitable waveform and frequency. According to example aspects of the present disclosure, the evaluation circuit has an output configured to supply the output signal, at least by measuring the voltage across the capacitor arrangement. The voltage is therefore measured across the capacitor arrangement during or after excitation. The measurement, or respectively evaluation can for example include the phase of the voltage; however, the voltage level can be measured, in particular the peak value of the voltage.

In the method according to example aspects of the present disclosure, the liquid is accommodated in the inner chamber in which the capacitor arrangement is arranged, or it flows through it so that liquid is arranged between the capacitor surfaces. A voltage across the capacitor arrangement, or respectively a measuring capacitance is measured, and based on this, an output signal is generated that depends on properties of the liquid.

The device according to example embodiments of the present disclosure and the method according to example embodiments of the present disclosure therefore allow properties of the liquid accommodated in the inner chamber or flowing through it to be determined by evaluating electrical properties, i.e., for example according to a purely capacitive measuring principle, and/or by detecting properties of a complex impedance of which a measuring capacitance represents a part. Opposing capacitor surfaces of the capacitor arrangement form at least one measuring capacitance, wherein the liquid in the gap between the capacitor surfaces functions as a dielectric. Accordingly, the capacitance value of the measuring capacitance, and therefore of the capacitor arrangement, depend on the dielectric properties of the liquid that may deviate depending on the composition and type of the liquid. Accordingly, for example, a portion of water in oil that is arranged between the capacitor surfaces can be recognized.

By connecting the capacitor arrangement as an RC element and exciting with an AC voltage, highly accurate detection can be achieved with very simple means so that it is possible to even ascertain for example very small amounts of water in oil.

According to example aspects of the present disclosure, the series circuit forms a low-pass filter, and the frequency of the exciting AC voltage lies in the region of the cutoff frequency of the low-pass filter, such as close to the cutoff frequency. In the simplest case of an RC element, the cutoff frequency is $f_C=1/(2\pi RC)$, as is known. In this case, when determining the cutoff frequency, the capacitance value C is considered while the measuring capacitance is being filled with pure liquid without impurities. Excitation "in the region of" the cutoff frequency can for example be understood as meaning that the frequency of the AC voltage lies within as the cutoff frequency. In some embodiments, the measuring frequency, i.e., the frequency of the exciting AC voltage, lies somewhat higher than the cutoff frequency. As is known, with an ideal low-pass filter, the output level at the cutoff frequency is about 70% of the input level. A suitable range for the excitation frequency "in the region of the cutoff frequency" could for example be considered a frequency range at which—only with reference to the RC low-pass filter and not to additional circuitry—the output level is between about 10% and about 90% of the input level, such as about 40-80%.

In some embodiments, the evaluation circuit has a peak value detector so that a peak value of the AC voltage can be determined using the capacitor arrangement. The determined peak value can be filtered by a low-pass filter and digitized in an analog/digital converter so that it can then be processed by a digital control unit. The processing can preferably be done by a program running on a processor. When using a sufficiently fast A/D converter, peak value detection can, if applicable, also be omitted, and the particular momentary value of the AC voltage can be directly evaluated via the capacitor arrangement.

The excitation circuit can be designed so that the AC voltage (excitation voltage) is applied continuously with a constant waveform and/or frequency. In some embodiments, the excitation voltage is a square wave voltage with a constant voltage value. Accordingly, the measuring capacitance is cyclically charged and discharged, limited by the measuring resistance. In an alternative embodiment, a square wave signal with a constant current can be used as the excitation signal.

According to example aspects of the present disclosure, the evaluation circuit can be designed to compare a peak value of the voltage across the capacitor arrangement with a threshold value. The comparison can be carried out in an analog circuit part, for example by means of a comparator, or by a digital circuit using a digitized value, in particular by a program that is executed on a computer processor. The threshold value can be fixed or determined dynamically. In one potential embodiment, the threshold value is established by a statistical analysis of measurements in a defined state, in particular when the interior is filled with a pure liquid without impurities.

According to example aspects of the present disclosure, two capacitor arrangements can each be provided as measuring capacitors in the inner chamber. A first capacitor arrangement with first capacitor surfaces is connected to the evaluation device which is designed to apply a first AC voltage to the series circuit including a first measuring resistor and the first capacitor arrangement. A second capacitor arrangement with spaced, opposing second capacitor surfaces in the chamber is also connected to the evaluation device so that it can supply an output signal that also depends on the capacitance of the second capacitor arrangement. For this, the evaluation device can for example be designed with two channels, in particular can have a second excitation circuit that is designed to apply a second AC voltage to a series circuit including a second measuring resistor and the second capacitor arrangement.

It is possible for the frequency of the first AC voltage and the second AC voltage to be the same. In some embodiments, however, the frequencies can also differ, i.e. the measurement by the first capacitor arrangement therefore uses a different excitation frequency than the measurement by the second capacitor arrangement. This can on the one hand serve to enable a redundant sensor device, wherein operation at different frequencies reduces mutual influence on the one hand and, on the other hand, ensures that the two measurements are not influenced by interferences in the same way. As will be explained below with respect to example embodiments, one of the two measurements can also be used to normalize the other measurement. Particularly, at least the first frequency can be chosen so that it lies above the cutoff frequency of the low-pass filter including the first measuring resistor and the first capacitor arrangement.

In some embodiments, the capacitor arrangement has a plurality of pairs of spaced opposing capacitor surfaces that each form measuring capacitances. The measuring capacitors can be electrically connected to each other such that they are electrically connected in parallel. The individual measuring capacitors can therefore be interconnected into a common, combined measuring capacitance. On the one hand, this increases the capacitance value which is good for the evaluation. On the other hand, a relatively large part of the inner chamber can therefore be captured simultaneously by ascertaining the capacitance value of the combined measuring capacitance.

In some embodiments, the capacitor surfaces can be formed as conductor surfaces on circuit board sections. In so doing, congruent conductor surfaces can be provided on the front and rear side of one or all circuit board sections that are short-circuited by a direct electrical connection, i.e., kept at the same electrical potential. Accordingly, the material of the circuit board section does not function as a dielectric and does not influence the measurement.

In some embodiments, the capacitor arrangement can have a circuit board structure with several rigid circuit board sections which are each connected by flexible conductor track carrier sections. This is a flat, electrically nonconductive support material with electrically conductive conductor structures applied thereupon. In particular, suitable plastic materials can serve as the support material. The rigid circuit board sections include epoxide resin with a glass fiber fabric, in particular FR4. The flexible conductor track carrier sections are ductile and can for example consist of polyimide. Conductor surfaces can be arranged on the rigid circuit board sections that form the capacitor surfaces. The conductor surfaces can include conductive material such as metal, such as copper. The flexible conductor track carrier sections can have tracks that are connected electrically to the capacitor surfaces.

When a circuit board structure with rigid circuit board sections and flexible conductor track carrier sections is used, there is a certain risk of a line break, in particular in the region of the flexible conductor track carrier sections. To be able to identify any damage to the flexible conductor track carrier sections, a circuit can be provided for recognizing a line break. This can in particular be connected to at least one conductor track that runs along an edge of a flexible conductor track carrier section since damage is naturally most likely to be feared in the edge region. Particularly, the conductor tracks are correspondingly connected and therefore monitored on both sides of the flexible conductor track carrier sections running at the edge.

According to example embodiments of the present disclosure, a detection element can be arranged on one of the rigid circuit board sections. Such a detection element can be designed in such a way that it is recognizable by its electrical properties so that its electrical connection, or respectively the disconnection thereof, can be determined with a suitable detection circuit. Particularly, the detection element can be a detection resistor that, in some embodiments, can be electrically connected in parallel to the capacitor arrangement. The evaluation circuit can have be configured to recognize whether the detection resistor is or is not connected. Accordingly, damage can be recognized in that an electrical connection of the evaluation circuit to the detection resistor is interrupted.

In some embodiments, the detection element can be connected to the evaluation circuit via a conduction path that extends over all flexible conductor track carrier sections. The integrity of all conductor track carrier sections is thereby checked.

FIG. 1 shows a schematic representation of a sensor device 10 according to a first embodiment. A housing 12 with an inner chamber 14 is provided for accommodating a liquid that flows into an inlet 16, flows through the interior 14, and is discharged through an outlet 18.

The liquid can for example be oil in which unknown portions of water in the form of individual droplets can be contained as impurities. The sensor device 10 serves to detect any water content and output an output signal A that indicates the presence of water content.

This is accomplished according to a primarily capacitive measuring principle, wherein however a relevant measuring capacitance, as presented below, can also be part of a complex impedance, and other components of the complex impedance can be detected while measuring, or respectively detecting.

A capacitor arrangement 20 is arranged in the inner chamber 14. The capacitor arrangement 20 comprises a first measuring capacitance 22 formed from two capacitor surfaces 24a, 24b facing each other across a gap 27, and a second measuring capacitance 26 formed from capacitor surfaces 28a, 28b that are arranged at the same distance from each other across the gap 27.

The liquid (oil) arranged in the gap 27 therefore forms the dielectric of the two measuring capacitances 22, 26. The capacitance value C1, C2 of the measuring capacitances 22, 26 depends on the properties of the liquid, in particular on any impurity, in this case for example by water droplets. The permittivity of oil is significantly lower than the permittivity of water so that the water droplets which flow through the gap 27 causes an increase in the capacitance values C1, C2 of the measuring capacitances 22, 26. Likewise, other components in the liquid that have dielectric properties deviating from the pure liquid can cause a detectable change.

The measuring capacitances 22, 26 in the direction of flow from the inlet 16 to the outlet 18 are arranged one after the other so that the fluid and the impurities transported therein can flow through them sequentially. Moreover, the measuring capacitances 22, 26 are arranged in the path of flow such that at least basically the entire liquid flow flows through the gap 27. This ensures that water components flowing through sequentially change the capacitance value of both measuring capacitors 22, 26.

The measuring capacitances 22, 26 are connected to an evaluation device 30 that, at given measuring intervals, determines a capacitance value C1 for the first measuring capacitance 22, and a capacitance value C2 for the second measuring capacitance 26 and, depending on the ascertained capacitance values C1, C2, emits the output signal A which indicates that a threshold value of the water content in the flowing oil has been exceeded.

Figure 2:
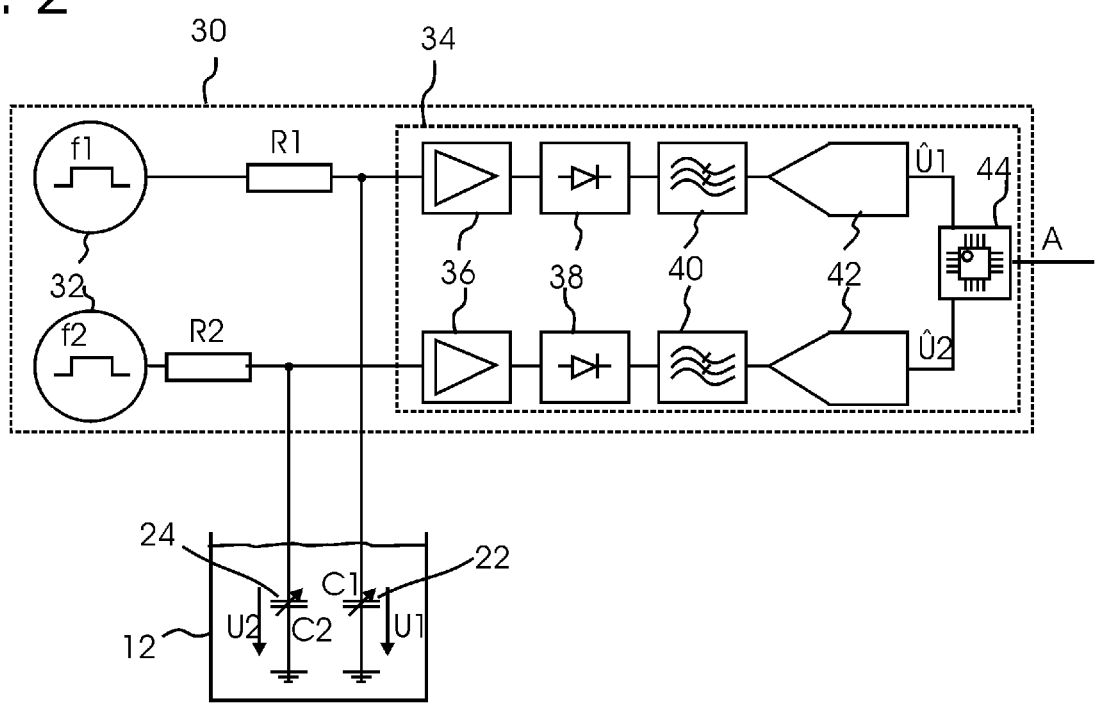
FIG. 2 depicts a schematic diagram of an evaluation circuit according to example embodiments of the present disclosure.

FIG. 2, in a schematic block diagram, shows functional elements of the evaluation device 30 that are connected to the measuring capacitances 22, 24. The evaluation device is designed with two channels, i.e., a separate channel is provided for each of the measuring capacitances 22, 24 and includes an excitation circuit 32 that is connected to a series circuit including a particular measuring resistor R1, R2 and the particular measuring capacitances 22, 24, and a channel of an evaluation circuit 34 that generates the output signal A.

Each measuring channel of the evaluation circuit 34 is connected to one of the measuring capacitances 22, 24 in order to determine their particular capacitance value C1, C2. Therefore, it has a buffer amplifier 36, a peak value detector 38, a low-pass filter 40 and an A/D converter 42 for each measuring channel. The two A/D converters 42 are connected to a processor 44 on which a program is executed that processes signals Û1, Û2 from the A/D converter 42 and generates the output signal A therefrom.

The first and second measuring capacitances 22, 24 are each connected to the respective measuring resistor R1, R2 as an RC element so that a complex impedance is formed which is excited by the associated excitation circuit 32 with a square wave signal of a frequency f1, f2. The excitation frequencies f1, f2 of the two measuring channels differ from each other. As a result, the respective capacity C1, C2 is cyclically charged and discharged by the respective measuring resistor R1, R2. Given a fixed time sequence, the voltage U2 resulting via the respective measuring capacitances 22, 24 is dependent on the capacitance value C1, C2.

The particular voltage signal U1, U2 is measured in the evaluation circuit 34, digitized, and processed. It is first buffered by the buffer amplifier 36. Its peak value is ascertained by the peak value detector 38 and evaluated-filtered by the low-pass filter 40—by the A/D converter 42 as a digital signal that is fed to the processor 44.

Figure 7:
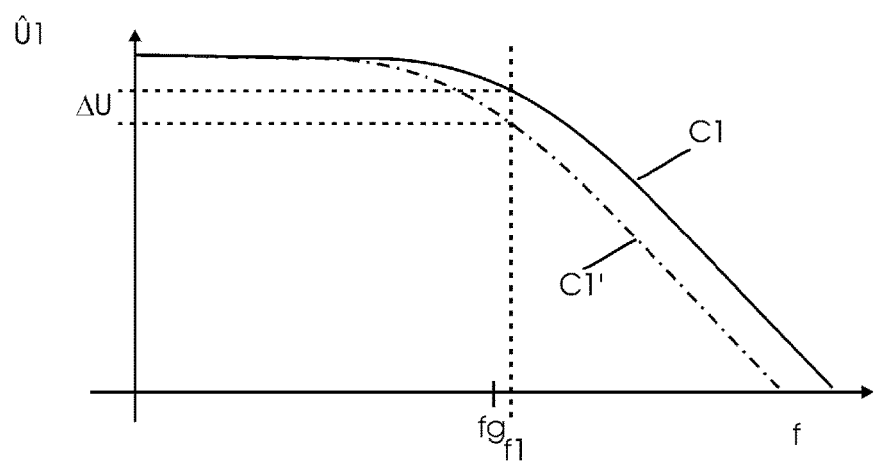
FIG. 7 depicts a diagram with a depiction of voltage signals depending on an excitation frequency relative to an ideal low-pass filter according to example embodiments of the present disclosure.

The respective RC element at both measuring channels functions as a low-pass filter. FIG. 7 shows the curve of the output voltage U1 depending on the frequency f as an example of the first measuring capacitor 22—idealized and double logarithmic. As shown therein, the curve of the peak value of the output voltage Û1 shown as a solid line results for a fixed capacitance value C1 (corresponding for example to the capacitance value of the first measuring capacitance 22 filled with liquid without impurities) when excited by different frequencies f. Significantly below the cutoff frequency $f_G = 1/(2\pi\, R1C1)$, there is basically no damping and an essentially constant curve of the peak value of the output voltage Û1. Around the cutoff frequency $f_G$, a voltage value Û1 results that decreases with the damping curve toward higher frequencies f.

However, the cutoff frequency fa is dependent on the capacitance value C1 and therefore on the properties of the liquid, in this case, especially on the portion of potential water impurities in the flow of oil. Due to water content, the capacitance C1 increases to an increased capacitance C1', so that the cutoff frequency $f_G$ decreases. In FIG. 7, the dot-dashed line shows the curve of the peak value of the output voltage Û1 over various frequencies f for a slight water content in the gap 27. As shown therein, the curve is shifted to the left in comparison to conditions without impurities.

Accordingly, given a fixed frequency f1, there is a difference in the output signal Û1 from the change of the capacitance C1 to the capacitance C1'. To achieve adequate sensor sensitivity, the measuring frequency f1 is chosen so that a clear difference AU is indicated when there is a change in capacitance. As is known, the output signal level at the cutoff frequency fg is about 70%. The measuring frequency f1 can for example be chosen so that the output signal level is between about 90% and about 10% (in each case given a fixed capacitance C1 without contamination). As used herein, the use of the term "about" in conjunction with a numerical value refers to within 10% of the stated amount.

When the measuring frequency, or respectively excitation frequency, f1 of the first channel of the evaluation device 30 is appropriately chosen, a variable output signal Û1 then results depending on whether there is pure liquid (oil) without water content or a certain portion of water droplets in the gap 27. Likewise, other kinds of impurities such as for example metal chips cause a change in the complex impedance, which is discernible from a changed output signal.

The two separate measuring capacitances 22, 24 and each of the assigned channels of the evaluation circuit 30 therefore supply signals Û1, Û2 in digital form to the processor 40. The two signals Û1, Û2 are processed by an evaluation program executed by the processor 44 to generate the output signal A.

This includes on the one hand a decision as to whether the respective signal Û1, Û2 manifests a deviation that indicates water content in the flowing oil. On the other hand, the processing can also include an analysis of the respective signal to identify potential error states.

In some embodiments, the evaluation program executed by the processor 44 per-forms a threshold value comparison for at least one of the signals Û1, Û2, wherein when a previously set threshold is undershot, a change is detected such that a contamination of the oil by water is indicated in the output signal A. The respective threshold can on the one hand be specified according to previous calculations or, on the other hand, ascertained by measurements and possibly statistical evaluations.

Accordingly, for example in a new state in which one can assume that only pure oil is in the gap 27, a frequency distribution of a plurality of measurements can be recorded, and thus for example the statistical parameters of a standard distribution (average, standard deviation, sigma) can be ascertained. Depending thereupon, the decision threshold can then be established for example as an average minus n*Sigma, wherein the factor n is to be appropriately selected so that, on the one hand, sufficient sensitivity is achieved and, on the other hand, sufficient robustness against false detections remains guaranteed.

When the sensor device 10 is operating, the two channels of the evaluation device 30 can be operated with the same or different frequencies f1, f2. In an embodiment with the same frequencies f1, f2, crosstalk can arise between the channels in certain circumstances; frequencies that at least slightly differ from each other may therefore be implemented. Both frequencies f1, f2 can be in the range of the cutoff frequency of the particular RC element (wherein the capacitance C without impurities is significant). The signals Û1, Û2 from the two channels can each be independently used for a separate measurement and detection of significant impurities. The detection of the two channels can then be analyzed so that, for example, the presence of an impurity is only signaled if impurities are simultaneously detected in both channels.

In alternative embodiments, the frequencies f1, f2 can also deviate more strongly from each other. For example, the first channel connected to the first measuring capacitance 22 can be operated at a frequency f1 in the range of the cutoff frequency of the particular R1C1 element (wherein the capacitance C1 without impurities is also significant in this case). The second channel connected to the second measuring capacitance 24 is then for example operated at an excitation frequency f2 significantly below the excitation frequency f1 and also below the cutoff frequency, i.e., in ranges in which the curves shown in FIG. 7 have no or little changes with the frequency. In in this case, the signal Û2 created in the second channel can be used to normalize the signal Û1, for example taking the difference or forming the ratio of the two signals.

In addition, it is noted that the capacitance values C1, C2 are temperature-dependent. A temperature sensor (not shown) can be arranged in the inner chamber 14 of the housing 12 whose measuring signal is also fed to the processor 44. The evaluation program then takes into account a compensation curve that has been previously calculated or experimentally ascertained depending on the temperature signal.

Whereas the above-described first embodiment of the sensor device only forms the basic form, various other embodiments are possible. In the following, a second embodiment of a sensor device will be described with reference to FIG. 3, FIG. 4a and FIG. 4b. The second embodiment provides a special arrangement of capacitor surfaces of the measuring capacitances 22, 26 in the inner chamber 14 of the housing 12 as will be explained below in detail. In all other respects, however, the sensor device according to the second embodiment corresponds to the above-describe sensor device 10 according to the first embodiment, in particular with respect to the evaluation device 30. In the following, the differences between the embodiments will therefore be explained, wherein identical reference signs will be used for the same or directly comparable elements.

FIG. 4a, 4b show a cross-section and longitudinal section of a part of a sensor device 110 according to the second embodiment. This includes a two-part housing 12 with a housing top part 12a and a housing bottom part 12b, between which the inner chamber 14 is formed. A capacitor arrangement 120 is arranged in the inner chamber 14. Each of the housing halves 12a, 12b has a holding structure 60 with holding elements 62 projecting in the direction of the inner chamber 14 and slots 64 formed therebetween.

FIG. 3 shows a part of the condenser arrangement 120. It includes a circuit board structure with several rigid circuit board sections 52a, 52b-five in the shown example—that are each connected by flexible conductor track carrier sections 54 into a chain. The rigid circuit board sections 52a, 52b are for example routine FR4 printed circuit boards that are flexible conductor track carrier sections 54, such as polyimide strips.

The flexible conductor track carrier sections 54 are each attached to the edges 58 of the rigid circuit board sections 52a, 52b and are fixed thereto. The flexible conductor track carrier sections 54 in the shown embodiment are arranged not in the middle but at the border of the respective edge 58. The flexible conductor track carrier sections 54 are lesser in width in comparison to the length of the edges 58 so that most of the length of the edges 58 remains free, and the corresponding regions of the rigid circuit board sections 52a, 52b can be used for fastening, as will be explained further below.

Large conductor surfaces 24a, 24b, 28a, 28b are arranged on each of the rigid circuit board sections 52a, 52b on both sides. Two conductor surfaces 24a, 28a, or respectively 24b, 28b are arranged next to each other on the front and back side of each of the rigid circuit board sections 52a, 52b. The conductor surfaces 24a, 24b, 28a, 28b are formed like the conductor tracks 56 on the flexible conductor track carrier sections 54 and the conductor tracks on the rigid circuit board sections 52a, 52b and as copper layers. The conductor tracks connect the conductor surfaces 24a, 24b, 28a, 28b electrically as schematically shown in FIG. 5.

To be arranged in the inner chamber 14, the circuit board structure of the capacitor arrangement 120 is folded so that the rigid PCB sections 52a, 52b are each arranged in parallel at a distance from each other, and the conductor surfaces 24a, 24b, 28a, 28b function as capacitor surfaces and form measuring capacitances across the gaps arranged therebetween.

The circuit board structure of the capacitor arrangement 120 is held in the folded arrangement within the housing 12 in that the edges 58 of the rigid circuit board sections 52a, 52b are each inserted into the slots 64 of the holding structure 60 where they are accommodated in a tight fit and are fixed both by the holding elements 62 as well as the holding pins penetrating the rigid circuit board sections 52*a*, 52*b*. As shown in FIG. 4*b*, however, only the free sections of the edges 58, i.e., not occupied by the flexible conductor track carrier sections 54, are accommodated in the slots 64 so that the flexible conductor track carrier sections 54 are not clamped.

Figure 5:
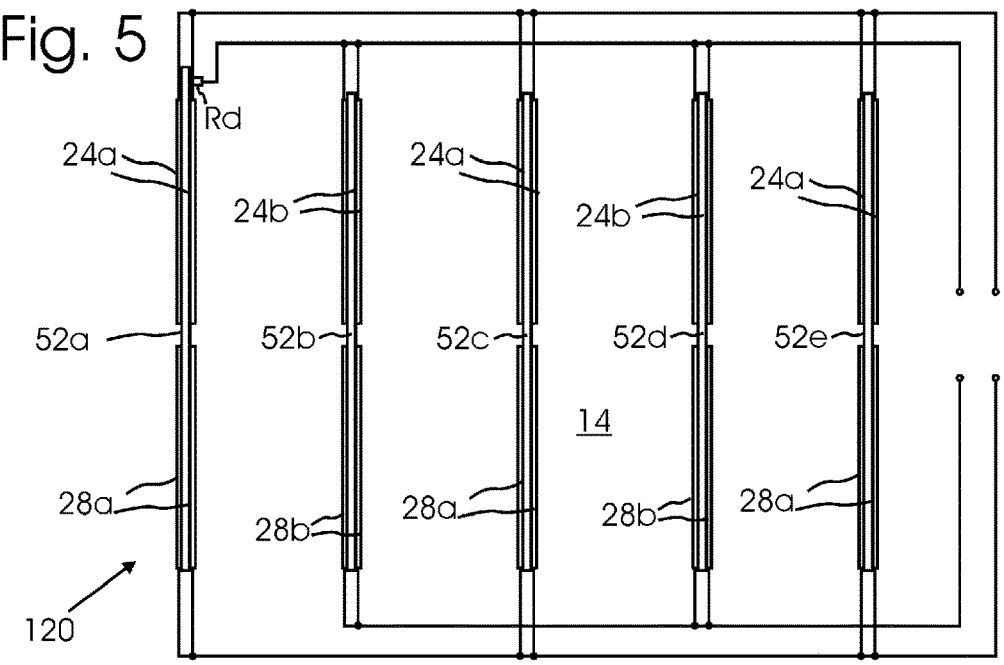
FIG. 5 depicts a schematic representation of a circuit diagram of the electrical configuration of the PCB structure of the sensor device of FIGS. 4a and 4b according to example embodiments of the present disclosure.

As schematically shown in FIG. 5, the conductor surfaces 24*a*, 24*b*; 28*a*, 28*b* applied on both sides of the rigid circuit board sections 52*a*, 52*b* are electrically short-circuited, i.e., the conductor surfaces on the front and back side are always at the same electrical potential. As already explained, opposing conductor surfaces 24*a*, 24*b*; 28*a*, 28*b* form measuring capacitances across the gaps arranged therebetween, wherein the liquid accommodated in the inner chamber 14 forms the dielectric. The direct electrical connection of the conductor surfaces 24*a*, 24*b*; 28*a*, 28*b* on both sides ensures that the material of the rigid circuit board sections 52*a*, 52*b* does not form a dielectric of the measuring capacitances and therefore does not have any influence on the measurement.

As moreover shown in FIG. 5, the individual measuring capacitances are connected in parallel so that two combined measuring capacitances are formed that each of which covers all of the gaps and therefore the entire inner chamber 14. As shown in FIG. 1 for the basic embodiment, the two combined measuring capacitors are arranged sequentially between the inlet and outlet (not shown).

Figure 6A:
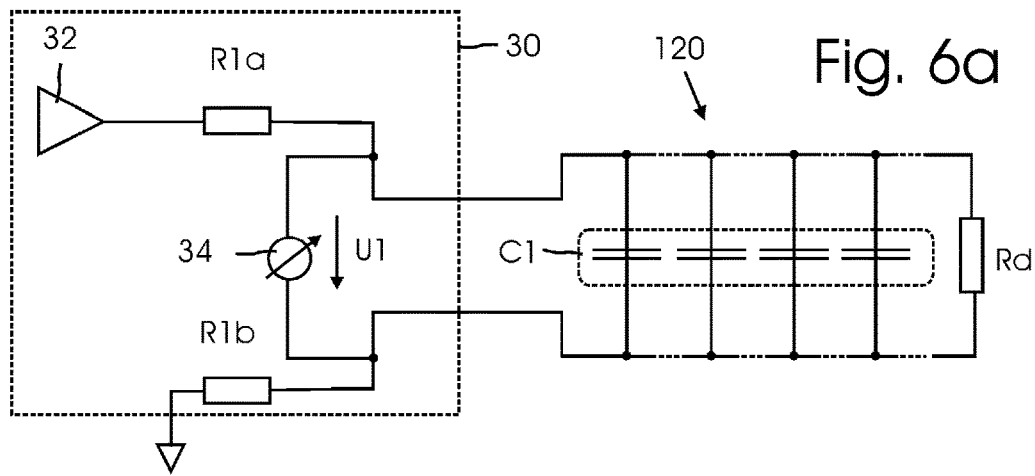
FIGS. 6a and 6b depict circuit diagrams of example embodiments for connecting the PCB structure of FIGS. 3-5 according to example embodiments of the present disclosure.

FIG. 6*a* shows a first version of the connection of the capacitor arrangement 120 to the evaluation device 30. As already explained with respect to FIG. 2, the combined measuring capacitor C1 is connected in series by a resistance element to the excitation circuit 32. A complex impedance can, for example, be formed in various ways in that the resistance element Ria is arranged in front of the measuring capacitance from the per-spective of the excitation circuit 32, or alternatively behind it (resistance element Rib), or both shown resistance elements Ria, Rib can be provided.

Figure 6B:
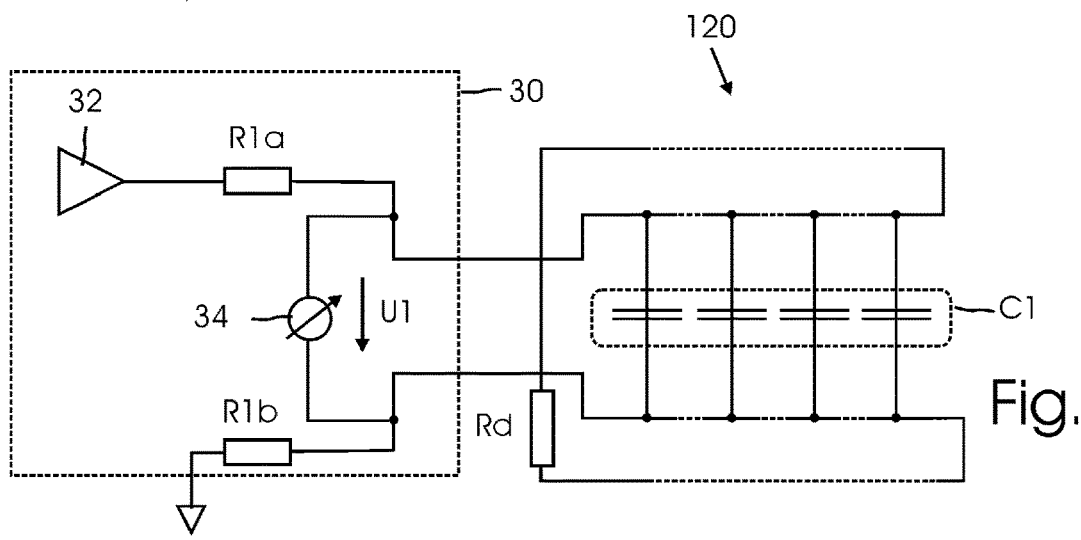

In addition, to detect line interruptions, in particular in the region of the flexible conductor track carrier sections 54, a conductor loop can be formed over all rigid circuit board sections 52*a*, 52*b* and over all flexible conductor track carrier sections 54 by connecting in parallel a detection resistor Rd to the measuring capacitance C1. The detection resistor Rd can be arranged on the last rigid circuit board section 52*a*, 52*b* as shown in the first version according to FIG. 6*a*, or in another location, for example on the first rigid circuit board section 52*a* as shown in the second version according to FIG. 6*b*. In any case, a conductor loop containing the detection resistor Rd is formed over all the flexible conductor track carrier sections 54, wherein in some cases, the conductor tracks of the conductor loop each run along the two edges of the flexible conductor track carrier sections 54 so that they are monitored in a special way.

A complex impedance is formed by connecting in parallel the detection resistor Rd to the combined measuring capacitance C1, in combination with connecting in series to the resistance elements Ria and/or Rib. The evaluation is nonetheless carried out as explained above, wherein however when the conductor loop is no longer connected to the detection resistor Rd because of a line break, this is recognized by the evaluation device 30.

Figure 8:
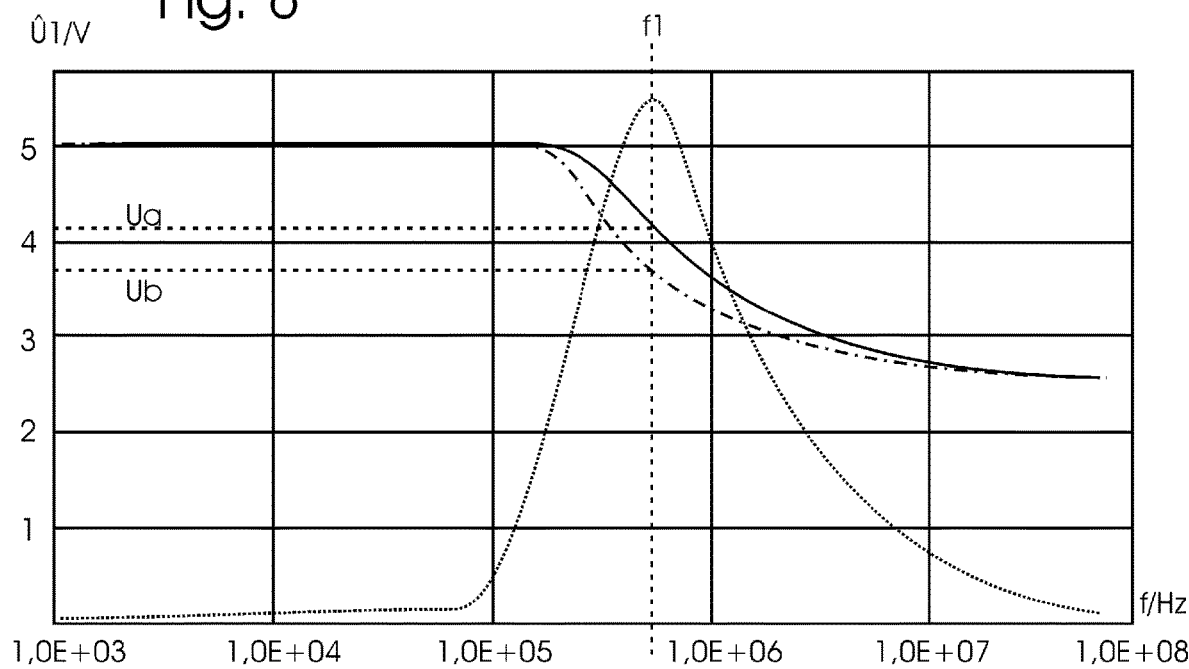
FIG. 8 depicts a diagram with a depiction of voltage signals depending on an excitation frequency related to the PCB of FIGS. 5, 6a, and 6b according to example embodiments of the present disclosure.

For the complex impedance that is formed by R1*a*/R1*b*, the capacitance C1 and the detection resistor Rd, FIG. 8 shows an example of the curve of the output voltage U1 depending on the frequency f. For a capacitance value C1 (without impurities), the frequency response with a cutoff frequency for example at $f_G=1/(2\pi\ R1C1)$ shown with a solid line results, whereas the frequency response shown with a dot-dashed line results when there is water content in the gap 27 with a lower cutoff frequency, i.e., as a curve shifted to the left in comparison to conditions without impurities.

The respective, frequency-dependent difference of the output signals between the relevant instance of liquid without impurities (solid line) and the liquid with water droplets (dot-dashed line) is shown as a dotted line. The difference curve forms a maximum in the region slightly above the cutoff frequency fa for the instance without impurities.

This frequency at which the voltage difference is at a maximum which arises depending on the change in capacitance is used as the excitation frequency $f_1$ of the first channel of the evaluation device 30. As plotted for example in FIG. 8, an output voltage Ua arises at this measuring frequency $f_1$ when there is liquid without water content, whereas the output voltage Ub results when there is a certain portion of water droplets.

Whereas the frequency response is variable in the range of the cutoff frequency as shown, the signal curves significantly above, or respectively below the cutoff frequency are very flat. The voltage values U1 at low frequencies (about 5 V in the example of FIG. 8) and at high frequencies (about 2.7 V in the example of FIG. 8), are inter alia determined by the detection resistor Rd. Voltage values significantly outside of the voltage range limited in this way (2.7-5 V in the example) accordingly indicate an error state, i.e., such as a short-circuit or line break. This is easily discernible by an evaluation program executed by a processor 44.

It is noted that the present disclosure is not restricted to the described embodiments and versions; instead, other embodiments are possible. Accordingly, for example, only a single measuring capacitance or several measuring capacitances can be provided instead of two measuring capacitances 22, 26. A different number of rigid circuit board sections 52*a*, 52*b* can also be provided, for example. Instead of signal evaluation with peak value detection, the particular momentary value can also be evaluated by using 10 faster A/D converters. In general, the features of the embodiments and the claims can be combined as desired.

The invention claimed is:

1. A sensor device having:
    an inner chamber for accommodating a liquid,
    a capacitor arrangement in the inner chamber, wherein the capacitor arrangement has spaced, opposing capacitor surfaces so that at least part of the liquid accommodated in the inner chamber is arranged between the capacitor surfaces,
    an evaluation device for supplying an output signal that is at least dependent on a capacitance value of the capacitor arrangement, wherein the evaluation device comprises an excitation circuit and an evaluation circuit,
    wherein the excitation circuit has at least one measuring resistor and AC voltage source configured to apply an AC voltage to a series circuit including the measuring resistor and the capacitor arrangement,
    wherein the series circuit including the measuring resistor and the capacitor arrangement forms a low-pass filter, and the AC voltage is applied at a frequency in a region of a cutoff frequency of the low-pass filter; and
    wherein the evaluation circuit has an output configured to supply the output signal by measuring a voltage across the capacitor arrangement.

2. The sensor device according to claim 1, wherein the cutoff frequency of the AC voltage is higher than the cutoff frequency.

3. The sensor device according to claim 1, wherein the frequency of the AC voltage is such that an output level of the low-pass filter is between about 10% and about 90% of an input level of the low-pass filter.

4. The sensor device according to claim 1, wherein the evaluation circuit is configured to compare a peak value of a voltage across the capacitor arrangement with a threshold value.

5. The sensor device according to claim 1, wherein:
the capacitor arrangement is a first capacitor arrangement with first capacitor surfaces, and the evaluation device is a first evaluation device with a first excitation circuit that applies a first AC voltage to the series circuit including a first measuring resistor and the first capacitor arrangement, and
in the inner chamber, a second capacitor arrangement is arranged with spaced, opposing second capacitor surfaces,
wherein the evaluation device for supplying an output signal dependent on a capacitance value of the second capacitor arrangement has a second excitation circuit configured to apply a second AC voltage to a series circuit including a second measuring resistor and the second capacitor arrangement,
wherein the first AC voltage has a first frequency, and the second AC voltage has a second frequency,
wherein the first frequency differs from the second frequency.

6. The sensor device according to claim 1, wherein the capacitor arrangement has a plurality of pairs of spaced, opposing capacitor surfaces that each form measuring capacitances, wherein the measuring capacitances are connected to each other such that they are electrically connected in parallel.

7. The sensor device according to claim 1, wherein at least one of the capacitor surfaces is formed as a conductor surface on at least a portion of a circuit board.

8. The sensor device according to claim 7, wherein:
a first conductor surface is arranged on a first side of the circuit board, and a second conductor surface is arranged on an opposite second side,
wherein the first conductor surface and the second conductor surface are at the same electrical potential by direct electrical connection.

9. The sensor device according to claim 1, wherein:
the capacitor arrangement has a circuit board structure with several rigid circuit board sections which are each connected by flexible conductor track carrier sections,
wherein conductor surfaces that form the capacitor surfaces are arranged on the rigid circuit board sections, and
wherein the flexible conductor track carrier sections have conductor tracks that are connected electrically to the capacitor surfaces.

10. The sensor device according to claim 9, wherein:
a detection element is arranged on at least one of the rigid circuit board sections, and
the evaluation circuit is configured to detect whether the detection element is connected to the evaluation circuit.

11. The sensor device according to claim 10, wherein the detection element is a detection resistor that is electrically connected in parallel to the capacitor arrangement.

12. The sensor device according to claim 10, wherein the detection element is connected to the evaluation circuit via a conduction path that extends over all flexible conductor track carrier sections.

* * * * *